United States Patent [19]

Molin et al.

[11] Patent Number: 5,697,960
[45] Date of Patent: Dec. 16, 1997

[54] CONFIGURING AN IMPLANTABLE ACTIVE MEDICAL DEVICE BY ADJUSTING PARAMETERS

[75] Inventors: Renzo Dal Molin, Chatillon; Pascal Pons, Fontaine, both of France

[73] Assignee: Ela Medical S.A., Montrouge, France

[21] Appl. No.: 365,912

[22] Filed: Dec. 29, 1994

[30] Foreign Application Priority Data

Dec. 31, 1993 [FR] France .................. 93 15961

[51] Int. Cl.$^6$ ............................................. A61N 1/08
[52] U.S. Cl. ............................ 607/59; 607/31; 607/2; 128/898
[58] Field of Search ................. 607/30–32, 59, 607/60, 2, 4, 5, 31; 128/898

[56] References Cited

U.S. PATENT DOCUMENTS

| | | | |
|---|---|---|---|
| 4,131,884 | 12/1978 | Comer | 340/347 |
| 4,138,671 | 2/1979 | Comer et al. | 340/347 |
| 4,203,448 | 5/1980 | Keller, Jr. | 607/30 |
| 4,262,632 | 4/1981 | Hanton et al. | 607/30 |
| 4,364,006 | 12/1982 | Makabe et al. | 323/353 |
| 4,407,288 | 10/1983 | Langer et al. | 607/4 |
| 5,080,096 | 1/1992 | Hooper et al. | 607/30 |
| 5,083,563 | 1/1992 | Collins | 607/4 |
| 5,103,819 | 4/1992 | Baker et al. | 128/419 |
| 5,360,437 | 11/1994 | Thompson | 607/60 |

FOREIGN PATENT DOCUMENTS 599 072 A2  10/1993  European Pat. Off. ......... H03M 1/66

*Primary Examiner*—William E. Kamm
*Assistant Examiner*—Kennedy J. Schaetzle
*Attorney, Agent, or Firm*—Orrick, Herrington & Sutcliffe LLP

[57] ABSTRACT

A process to configure an implantable active medical device by adjusting a parameter. For each parameter to be adjusted, the steps of the process are: the determination of a code of adjustment for a given parameter value, writing of the code of adjustment to alter a circuit configuration, and the verification of the validity of the set code. A verified code is then permanently written by straining of selected diodes. The code of adjustment is thus used to adjust a circuit configuration to alter the sensed operating parameter value so that, after straining, the adjusted parameter value of the configured circuit falls in or at a desired range or value. Suitable circuit parameters include clock frequency and reference voltage levels, as are found in cardiac pacemakers and defibrillators.

44 Claims, 1 Drawing Sheet

CONFIGURING AN IMPLANTABLE ACTIVE MEDICAL DEVICE BY ADJUSTING PARAMETERS

FIELD OF THE INVENTION

The present invention concerns configuring an implantable active medical device by adjustment of circuit parameters, more particularly adjusting a circuit parameter of a cardiac control device.

BACKGROUND OF THE INVENTION

Implantable active medical devices include, for example, cardiac pacemakers and cardiac defibrillators. In order to ensure satisfactory functioning, these devices need precise or absolute electrical references. They need, for example, reference voltages that are particularly usable for the detection of cardiac activity.

Furthermore, the miniaturization of implantable active medical devices imposes the requirement that integrated circuits be used. However, the technological parameters linked to the manufacturing process that produces these integrated circuits are variable from one circuit to an other, and from one production batch of circuits to another. Consequently, these technological process fluctuations entail corresponding fluctuations of electrical parameter magnitudes provided by integrated circuits, such as occurs in the case of clock frequencies or reference voltages, for example.

To reduce the observed variations in performance (i.e., the difference between the actual performance and the desired performance, hereinafter referred to as a "dispersion"), which can be significant from one device to the next, it is necessary to proceed with an adjustment of parameter(s) in the course of the manufacturing process of the implantable active medical device. This adjustment can be external, by an action on the circuit, or internal, by an action on elements to a memory.

The external adjustment can be made by a dynamic adjustment of passive external components. For example, resistive chips can be adjusted (trimmed) by a laser beam or an etching machine. However, this type of external adjustment presents several disadvantages. First, the congestion of adjustment machines is excessive. Second, there exists a risk of interferences, e.g., working on the wrong portion of the circuit. Finally, the adjustable component types are essentially limited to resistances. The external adjustment also can be realized by wiring the integrated circuit to adjust the parameter value to a preselected value, but corresponding disadvantages are linked to the congestion and to difficulties of manufacture.

The internal adjustment can be realized by means of programming a memory such as a RAM. This, however presents the disadvantage that it is sensitive to variations of power supply and to external radiation. It can also be realized by a programmable memory that is electrically erasable, of the type EEPROM, whose disadvantage is sensitivity to radiation.

SUMMARY OF THE INVENTION

An object of the present invention is to propose a process of configuring an integrated circuit by adjustment of analog electrical parameters by means of programming numerical data.

Another object of the invention is to propose a process of configuration of an implantable active medical device by writing and possibly coding of its serial number for purpose of identification of the device.

Broadly, the present invention is directed to a process of configuring an implantable active medical device by adjustment of one or more circuit operating parameters by means of a stored code to reconfigure the circuit. One such method includes the steps of:

determining a code of configuration, which code is representative of the desired parameter value to be attained;

writing the code into an implantable active device by straining one or more diodes thereby to adjust the parameter value to the preselected value or within a preselected tolerance range; and verifying the validity of the code.

The term "straining" or "strained" as used herein refers to altering the normal function of a diode-type semiconductor junction by passing a current pulse to place the junction in an essentially homogenous state, e.g., a fixed resistance. This also is known as "Zener Zapping" when the diode is a zener diode. Thus the term straining is used in the same sense as blowing a fuse to form a high impedance open circuit-like state, or programming an antifuse device to a low impedance or closed circuit-like state, in that if the straining event is effective, the normal asymmetrical function of the semiconductor junction is irrevocably altered and the junction assumes a generally symmetrical fixed-impedance condition.

Preferably, the step of writing of the code by straining of diodes is realized by connecting the device to a source of external power.

Preferably, the step of determining the code of configuration comprises selecting the parameter to adjust, reading the value of the selected parameter, and determining, by means of a table or a software routine, a code of configuration corresponding to the sensed parameter value to write into the device to correct the dispersion.

For each parameter that is adjusted, there is associated a binary word whose length is a function of the value of the dispersion of the parameter read and the desired precision. Each bit of the binary word is associated with a parameter and has a corresponding diode. The state of the diode may be strained, corresponding to a 1 state of the bit, or functional, corresponding to a 0 state of said bit. The diode is used to switch selectively into the circuit of interest other circuit elements having values that will, by becoming connected to and a part of the structure of the circuit of interest, adjust the selected parameter value to the preselected value.

The step of writing the code of configuration preferably comprises the positioning of addresses of the bits to write, connecting the device diodes to at least one source of power, defining a voltage and a current intensity, the straining occurring by delivering a current pulse during a definite duration through the diode, and a verification of the straining by reading the bit written. The step of writing preferably comprises, in addition, in case of the straining not being effective, increasing the intensity of source current, repeating the operation of writing with the increased current intensity and testing again for an effective straining occurs. The sequence repeats until either a maximum current level is reached or an effective straining occurs.

The step of verification of the validity of the code comprises the reconfiguration of the implantable active medical device in a normal functioning condition, and checking the validity of each selected parameter value. In the preferred embodiment, a verification step also occurs before actually straining any diodes using the code of configuration to alter the circuit structure by switching in the selected circuit elements, as well as after the diodes have been strained by using the connections formed by the strained diodes to switch in the circuit elements. In this regard, the step of verification before straining occurs during the step of determining the code of configuration, which comprises in addition loading (i.e., temporarily storing) the code to set the register to cause the circuit to be configured in the adjusted manner, and verifying that the result is as desired. Further, if necessary, the selected code may be modified in response to a verification test that does not yield a good result, until the selected code of configuration results in a verification test that indicates a good selected parameter value. Once the good value is verified, then during the writing step the selected diodes corresponding to the appropriate bits of the verified loaded code are strained, and the straining is verified.

In one embodiment, the power source has a voltage on the order of volts, and a current intensity on the order of mA. More preferably, the voltage is +9V as compared to the source of negative polarity power, and the current intensity of 30 mA. The increment of current intensity of the current is 10 mA; and the increase of the current intensity of the current is typically limited to a value. For example, the predetermined limit value of the current intensity is 120 mA.

The diode is preferably a Zener diode. The diode also may be otherwise constituted, for example, by the emitter—base junction on a bipolar transistor whose collector—base junction is short-circuited.

The steps of determining, writing and verifying the code of configuration, are achievable during manufacture, as well as at the end of the process of manufacture. It is useful whether the case of the active implantable medical device is opened, or closed, respectively. Further, steps of determining, writing and verifying the code of configuration are achievable by telemetry and by connection of the device to at least one external power source.

Advantageously, an adjustment of an implantable active medical device in accordance with the present invention may occur under realistic operating conditions, prior to being implanted, and without having to open the case.

In one embodiment, the step of writing of the code implements two external power sources. One of the sources has a negative voltage and the other has a positive voltage. The external power sources are connected to the connectors of the implantable active device that are destined to receive leads, e.g., endocardial sensing or pacing leads, or defibrillation leads.

The invention also is directed to the application of the foregoing process to the functional configuration of a cardiac pacemaker, to the functional configuration of a cardiac defibrillator; and to the identification of an implantable active medical device by coding of its serial number.

BRIEF DESCRIPTION OF THE DRAWING

Further features of the invention, its nature and various advantages, will be more apparent from the accompany drawing and the following detailed description of the invention in which the FIGURE shows a circuit for an oscillator having an adjustable frequency based on a selective commutation of capacitance by a method in accordance with a preferred embodiment of the invention.

DETAILED DESCRIPTION OF THE INVENTION

Figure 1:
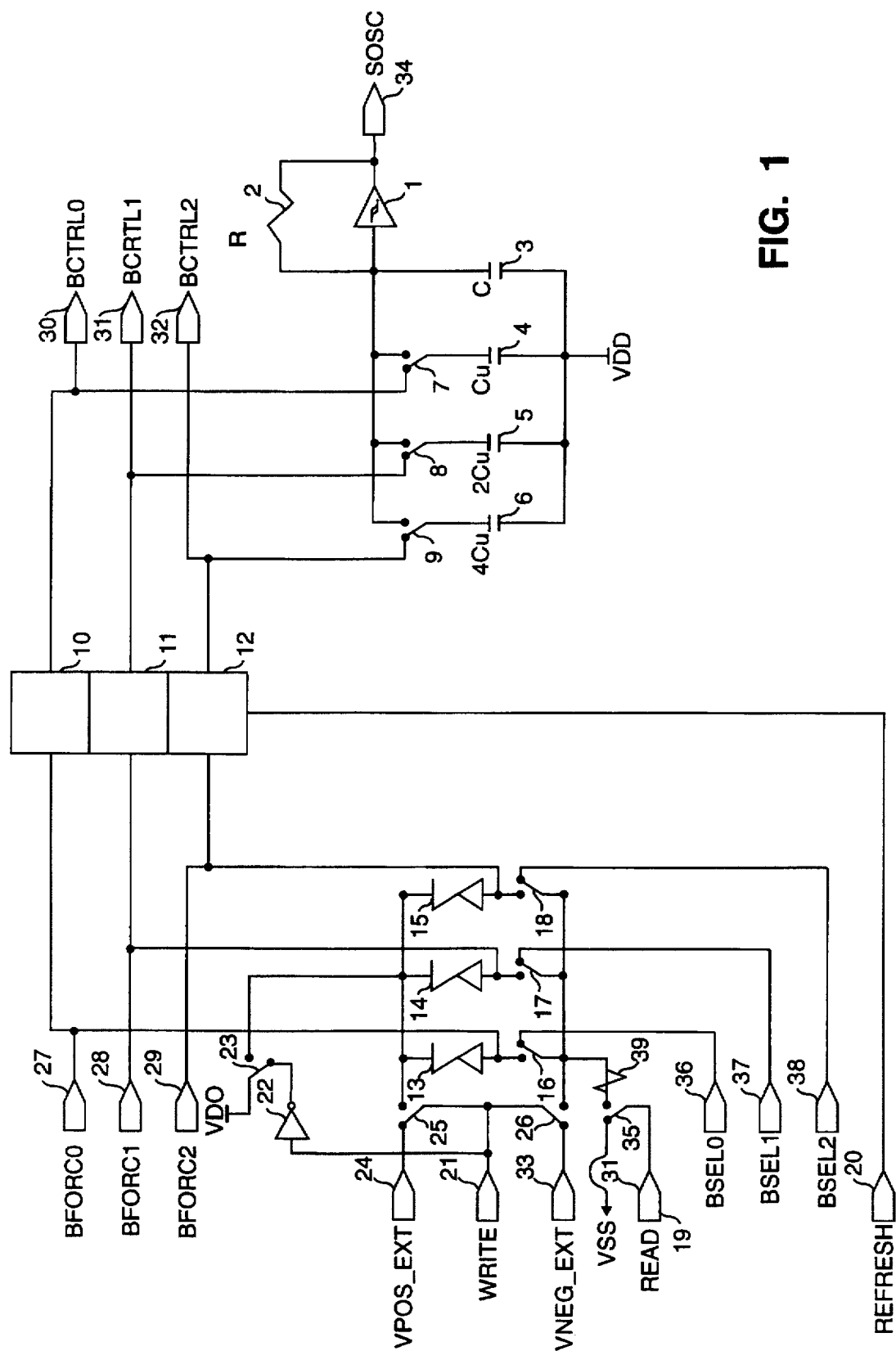

With reference to the Figure, a circuit having an electrical parameter to be adjusted by a method of the present invention is illustrated. It is noted on FIG. 1, the circuit is an oscillator having an integrated RC circuit, which includes an invertor 1 with hysteresis, a resistor 2 in parallel of value R, and a capacitor 3 of value C. In parallel with capacitor 3 are three capacitors 4, 5, 6, respective values of Cu, 2Cu, 4Cu. The three capacitors 4–6 are susceptible to be independently and selectively connected in parallel with the capacitor 3, or switched out of the circuit by three switches 7, 8, 9, each of which is controlled by a register 10, 11, 12 respectively. Each of these three registers 10, 11, 12 also is connected to a Zener diode, respectively 13, 14, 15, that is found in series with a switch, respectively 16, 17, 18. A common lead (pin) 19 for reading (READ) allows reading of the state of the diodes 13–15, and conducting the verification test. The READ lead 19, when it is activated, closes a switch 35 that, through a resistor 39, (for example, 90 K$\Omega$ so as to limit the current), connects the common negative voltage VSS to switches 16 to 18. A REFRESH lead 20 allows cyclic refreshment of registers 10 to 12.

The diodes 13 to 15 are normally connected to the general ground VDD by the intermediary of a switch 23. The switch 23 is controlled by the line 21 (WRITE) by the intermediary of invertor 22. The WRITE line 21 also controls directly, two switches 25 and 26 connecting respectively the diodes 13 to 15 to a source of positive external power 24 (VPOS-EXT) and switches 16 to 18 to a source of negative external power 33 (VNEG-EXT). Thus, when the signal on the write line 21 is low (0) the switch 23 is closed and switches 25 and 26 are opened, and when the signal is high (1) the switch 23 is opened, and switches 25 and 26 are closed. Switches 16 to 18 are controlled by a selection bus including lines 36 (BSEL0), 37 (BSEL1) and 38 (BSEL2), so as to activate the one corresponding diode to strain it or to verify the diode state. A loading bus including lines 27 (BFORC0), 28 (BFORC1) and 29 (BFORC2), loads a selected code of configuration in registers 10 to 12 to set the registers 10 to 12 according to the code bit values. This loading permits one to test the verification of the code of configuration, and whether it produces a parameter of acceptable dispersion, before the diodes are actually strained.

Once a code of configuration is loaded in registers 10–12 by loading bus 27, 28, 29 and verified as valid, the diodes may be strained. This occurs when the WRITE line 21 applies a high signal (1) and one of the diodes is selected to be strained by select bus 36, 37 and 38. As a result, the switch 23 opens, switches 25 and 26 close, and the selected one of diodes 13 to 15 to be strained is powered between the external power source 24 (VPOS-EXT) and the external power source of 33 (VNEG-EXT). These sources of power are for example of +4V and −5V respectively. The result is that the selected diode is submitted, for example, diode 13 when the select line 36 (BSEL0) is at a high level 1, to a voltage of 9V. This voltage is capable in principle to insure in several milliseconds the straining of the diode 13. Typically, only one diode is strained at a time. Thus, in this example, register 10 will remain set high (1) with only diode 13 strained, and insure the transmission of the control bit 1 to set switch7 of capacitor4 in a manner to insure, for example, the placement in parallel with the capacitor 3, only the capacitor 4 corresponding to the data in register 10. The other diodes 14 and 15 are not (yet) strained and thus registers 11 and 12 transmit the control bit 0 to switches 8 and 9 so that capacitors 5 and 6 are not in the circuit with capacitor 3. The other diodes then will be strained if appropriate according to the verified code, until all of the selected diodes are strained.

The outputs of registers 10, 11, 12 also are connected to a control bus comprising respectively lines 30 (BCTRL0), 31 (BCTRL1) and 32 (BCTRL2), allowing to proceed to the step of verification of the validity of the code of configuration prior to, and subsequent to straining.

According to the invention, there is for each electrical parameter to be adjusted, a word of a predetermined numerical length, that is to say to N bits (3 bits in the example of the FIG. 1). This number depends on the dispersion of the selected parameter value, which is specified by the manufacturer or the designer, and the desired precision. Each bit of the numerical word is then associated with a Zener diode. For convenience, the binary code (i.e., the bit value) associated with each diode is defined by convention: 0 for a functional diode, and 1 for a strained diode.

In the initial state, before writing, a functional state, an a functional state, and the bits of binary codes associated are all positioned to the value 0 (arbitrarily by convention). The step of writing the code of configuration, for the parameter adjustment, programming and identification is thus advantageously simplified by the fact that it is necessary to write only bits of value 1.

In practice, a Zener diode is essentially constituted by a semi-conductor emitter—base junction in a bipolar transistor whose collector—base junction is short-circuited. The straining of the diode is effected by elevation of the power, by means pulses of current of determined intensity and duration, for example, some tens of mA, during some ms, at some V. In the case of the circuit illustrated in the Figure, the straining can be achieved by current pulses of 30 mA during 2 ms at 9 V, for each of the diodes submitted to the straining.

When the straining is effective, a short-circuit appears by reason of the distribution of metallization through the junction. The diode is then converted to a resistance of some kiliohms. The codes of configuration are, therefore, obtained during the polarization of the diodes. This polarization is commutable by means the READ line 19 so as to minimize the power consumption. Codes are stored in registers, with cyclic refreshment by REFRESH line 20.

The procedure of adjustment of an electrical parameter has three phases. The first phase is the determination of the code of adjustment, e.g., in an enclosure at a regulated temperature of 37° C., preferably. This first phase comprises the selection of the analog parameter to control; reading the selected parameter value; determining, according to a look-up table or a software control algorithm, a code of configuration to be written relating to the general parameter value; loading the code to reconfigure and adjust temporarily the circuit parameter; and verifying the sensed parameter value according to the loaded code to be the correct preselected value of the parameter. If the loaded code is not valid, a new code is selected, loaded to set the registers and tested until a correct parameter value is obtained (or cannot be obtained, for example, when the circuit is too far out of tolerance to be corrected).

The look-up table or software control algorithm may be implemented in a conventional manner. One preferred embodiment includes determining the dispersion of the sensed parameter value relative to a preselected value, and associating the dispersion measure with a code that will switch in the circuit element values to cause the adjusted parameter value to be at the preselected value. In such case, the code reflects a magnitude of the dispersion that will operate to strain selected ones of diodes to minimize the dispersion, and, on the next evaluation, produce a dispersion of effectively zero.

The second phase is the writing of the code, which occurs by straining the appropriate diodes in response to a valid code. In this second phase, the writing of the code is made bit by bit, for each parameter to adjust in a sequence of operations comprising: setting of internal power supply of negative polarity to an external negative voltage (−5V, for example), the positioning of addresses of the bit to write, the connection to the source of positive polarity power (for example: V=+4 V and I=30 mA), writing by delivering the current pulse during 2 ms, disconnecting the sources, and verifying the straining by reading of the associated bit set. If the straining is not effective (i.e., not successful), the source current is increased by an amount of 10 mA, and the second phase of writing is repeated. The sequence of increasing the current if the writing is ineffective is repeated after each test, until either the straining is effective or an upper limit of the current intensity is reached, for example, 120 mA. This operation of writing of the code by straining selected ones of the diodes is made for the diodes corresponding to each code word bit of value 1, according to the above-described convention.

The third phase is the verification of the validity of the code after straining. This third phase of the procedure of adjustment comprises the reconfiguration of the pacemaker in its normal functioning condition, that is to say with a power of 2.8 V, for example, and checking the validity of each of the adjusted parameters.

In the embodiment shown in the Figure, one or several of the diodes 13 to 15 are subjected to straining. Corresponding switches 7 to 9, necessary for the commutation of capacitance, are therefore respectively positioned in one of the eight possible combinations so as to adjust the frequency of the oscillator.

The straining of integrated diodes presents several advantages as compared to the techniques previously known. It is an internal adjustment technique which is controllable from the exterior. The Zener diodes are integrated in the same chip with the other mixed or analog functions of the implantable active medical device, thus contributing to a minimal circuit congestion. This principle of adjustment does not entail an appreciable increase of the consumption of the implanted battery. Its irreversible character insures a great reliability and at the same time, an insensitivity to external perturbations such as radiation or electromagnetic interference. The adjustment can take accounts of dispersions linked to the construction of integrated circuits as well as to discrete components and their performance in a realistic (normal operating) environment corresponding to the temperature of the human body. As a result, a greater effective yield can be obtained in the integrated circuit manufacture.

The process of electrical parameter adjustment according to the invention is applicable in an implantable active medical device such as a cardiac pacemaker or a cardiac defibrillator to insure the adjustment of circuits such as clock frequencies, reference voltages, and currents, or signal processing circuits, for example, in the adjustment of the sensitivity or the dynamic range of operation. It is equally applicable to the adjustment of measuring circuits, notably for monitoring the power supply or monitoring signals sensed at a lead, to the programming of the model of a pacemaker, and to the selection of its modes of functioning. Advantageously, a basic integrated circuit structure can be formed which can be configured in accordance with the present invention to operate as one of a number of different circuits corresponding to different model pacemakers having different reference voltages, for example, or signal sensitivities or oscillator frequencies for other examples. The invention also is applicable to the coding of the identification of the implantable active medical device, for example, by a serial number.

This last step of identification and/or conformation of the implantable active medical device can occur at the end of the manufacturing process or even later, e.g., before implantation. In this case, all operations of determination, writing and verification of codes of configuration, programming and identification can be realized by telemetry, without consuming an incremental amount of energy from the internal battery (power supply). The connection of the external power sources is preferably obtained through by the connector of the device destined to receive leads.

One of ordinary skill in the art will appreciate that the present invention can be practiced other than by the foregoing embodiments, which are presented for purposes of illustration, and not of limitation.

We claim:

1. Process of configuring an implantable active medical device having a plurality of diodes by adjustment of circuit parameters by means of a code, comprising:
   determining a code of configuration;
   adjusting said parameters to a preselected value, wherein the step of adjusting comprises writing the code by straining of said diodes; and
   verifying the validity of the written code.

2. Process according to claim 1, wherein the step of writing the code by straining of said diodes is realized by connecting the device to at least one source of external power.

3. Process according to the claim 2, characterized in that the step of writing the code of configuration further comprises, addressing one bit of said binary word, wherein the connecting to said source of power further comprises defining a voltage and an intensity of current, wherein the writing of said code occurs during a definite duration, and wherein the verifying of said code further comprises reading the addressed bit to determine the validity of the straining of said diodes.

4. Process according to claim 3, characterized in that the step of writing further comprises, in the case of an ineffective straining, repeating the operation of writing after increasing the intensity of the current, by one increment after each straining of said diodes, until further effective straining occurs.

5. Process according to claim 4, characterized in that the increment of the current intensity is approximately 10 mA.

6. Process according to claim 4, characterized in that the increase of the current intensity further comprises limiting the current intensity to a predetermined value.

7. Process according to claim 6, characterized in that the predetermined value of the current intensity is approximately 120 mA.

8. Process according to claim 3, characterized in that the voltage of the source of power is measured in volts and the intensity of the current is measured in mA.

9. Process according to claim 8, characterized in that the voltage is approximately +9V as compared to a source of negative polarity power, and the current intensity is approximately 30 mA.

10. Process according to claim 2, characterized in that the step of writing of the code further comprises connecting at least two external power sources to the device.

11. Process according to claim 10, characterized in that one of the said sources is a negative voltage and the other is a positive voltage.

12. Process according to claim 10, characterized in that the sources of external power are connected to a connector of the implantable active medical device destined to receive a lead.

13. Process according to claim 1, wherein the step of determining the code of configuration comprises selecting the parameter to adjust, reading a circuit parameter value of said parameter, and determining, by application of one of a table and a software, the code of configuration to write.

14. Process according to claim 13, further comprising reading a dispersion value of said parameter to be adjusted and characterized in that each parameter to be adjusted has an associated binary word whose length is the function of a dispersion value of the parameter read and the desired precision.

15. Process according to claim 14, characterized in that each bit of the binary word associated to a parameter corresponds to a diode, whose functional or strained state corresponds to a 0 or 1 state of said bit.

16. Process according to claim 15, characterized in that the diode is a Zener diode.

17. Process according to claim 15, characterized in that the diode comprises an emitter—base junction on a bipolar transistor having a collector—base junction that is short-circuited.

18. Process according to claim 13, characterized in that the step of determining the code of configuration further comprises loading the code in the device and verifying that the code produces the preselected value of the parameter to be adjusted.

19. Process according to any of claims 1–3 characterized by providing the active implantable device with a case that is one of opened and closed, and characterized in that the steps of determining, writing and verifying the code of configuration are achievable with the active implantable device case being one of opened and closed.

20. Process according to claim 1, characterized in that the step of verification of the validity of the code comprises reconfiguring the implantable active medical device in a normal functioning condition and checking the validity of each of the adjusted parameters based on said preselected value.

21. Process according to any of claims 1 to 3, characterized in that the steps of determining, writing, and verifying of the code of configuration further comprise using telemetry to determine, write and verify the code of configuration and connecting the device to said external power source.

22. The process of claim 1 wherein the implantable active medical device is a cardiac pacemaker.

23. The process of claim 1 wherein the implantable active medical device is a cardiac defibrillator.

24. The process of claim 1 wherein the parameters further comprise at least one serial code and further comprising the step of identifying said device by said serial code.

25. Process according to claim 1, characterized in that the step of determining the code of configuration further comprises reading the code in the device and verifying that the code produces the preselected value to be adjusted.

26. A process for configuring a circuit of an implantable active medical device having a plurality diodes by adjusting a sensed circuit parameter, comprising the steps of:
   a) determining a code of configuration to adjust the sensed circuit parameter to a preselected value;
   b) writing the determined code by straining at least one of said diodes to achieve the adjustment of the circuit parameter; and
   c) verifying the validity of the written code.

27. The process of claim 26 wherein step b) further comprises:
   i) providing an external power supply;
   ii) connecting the at least one diode to said external power supply for a period of time; and iii) delivering a signal from said power supply at a first current intensity and a first voltage level for said period of time to strain the diode.

28. The process of claim 27 wherein step b) iii) further comprises delivering a signal having a current intensity measured in mA and a voltage measured in volts.

29. The process of claim 28 in which the implantable active medical device has an internal negative polarity power supply, wherein step b) iii) further comprises delivering a signal having a current intensity of approximately 30 mA and a voltage of approximately +9 volts relative to the negative polarity power supply.

30. The process of claim 26 wherein step a) further comprises:
   i) selecting a circuit parameter to be adjusted;
   ii) measuring a value of the circuit parameter; and
   iii) determining a code of configuration in response to the measured circuit parameter value, said code corresponding to a numerical code to adjust the selected circuit parameter value to a predetermined value.

31. The process of claim 30 wherein step a) iii) further comprises providing one of a look-up table and a software program to relate one of a plurality of measured parameter values to one of a plurality of codes of configuration.

32. The process of claim 30 wherein step a) ii) further comprises determining a dispersion value of the measured circuit parameter value, and step a) iii) further comprises providing each parameter to be adjusted with an associated binary word having a length that is a function of the determined dispersion value and a predetermined precision.

33. The process of claim 32 wherein providing a binary word further comprises providing each binary word with at least two bits and associating each bit with one diode.

34. The process of claim 33 wherein step b) further comprises addressing one bit of the binary word, connecting the corresponding one diode to an external power source for a period of time, and delivering a signal from said power supply at a first current intensity and a first voltage level for said period of time to strain the one selected diode corresponding to said addressed bit.

35. The process of claim 34 further comprising determining whether the straining was effective or ineffective, and in the case of an ineffective straining, increasing the current intensity by an increment and repeating step b) for straining said bit.

36. The process of claim 35 wherein the step of increasing the current intensity by an increment further comprises increasing the current intensity by approximately 10 mA.

37. The process of claim 35 wherein the step of increasing the current intensity by an increment further comprises increasing the current intensity one increment after each determination up to a maximum current intensity.

38. The process of claim 37 wherein the step of increasing the current intensity to a maximum current intensity further comprises increasing the current intensity to a maximum current intensity of approximately 120 mA.

39. The process of claim 26 further comprising the step of
   d) verifying the validity of the written code by configuring the implanted medical device to function in a normal operating condition, and determining whether or not the selected parameter has been adjusted to the preselected value.

40. The process of claim 26 wherein step a) further comprises the step of temporarily writing the determined code in the device and verifying whether or not the written code achieves the adjustment of the circuit parameter to the preselected value.

41. The process of claim 26 wherein step b) further comprises providing each diode as one of a zener diode and a semiconductor emitter to base junction of a bipolar transistor having a collector to base junction that is short circuited.

42. The process of claim 26 wherein step a) further comprises determining a code of configuration having a plurality of bits of a 0 or 1 state, and wherein step b) further comprises providing a plurality of diodes such that one diode corresponds to each bit, each diode having a functional state, and straining selected ones of said diodes to a nonfunctional state, said selected ones of diodes corresponding to the bits of said code having a 1 state.

43. The process of any of the claims 26, 39 40, 41 and 42 wherein step a) further comprises determining a code of configuration to adjust the circuit parameter to a preselected value for operation of the device according to one of a first model device and a second model device, said first and second model devices having different preselected values for said circuit parameter.

44. The process of any of the claims 26, 39, 40, 41 and 42 wherein step a) further comprises determining a code of configuration corresponding to a serial number for said device.

* * * * *

UNITED STATES PATENT AND TRADEMARK OFFICE
CERTIFICATE OF CORRECTION

PATENT NO. : 5,697,960
DATED : December 16, 1997
INVENTOR(S) : Dal Molin et al.

It is certified that error appears in the above-identified patent and that said Letters Patent is hereby corrected as shown below:

Column 1, line 24, delete "an other" and insert --another--;
Column 5, line 14, after "writing," insert --all the diodes are in--;
Column 5, lines 14-15, delete "on a functional state,"

Signed and Sealed this

Twenty-second Day of December, 1998

Attest:

BRUCE LEHMAN

Attesting Officer

Commissioner of Patents and Trademarks